US009440012B2

United States Patent
Miyakoshi et al.

(10) Patent No.: US 9,440,012 B2
(45) Date of Patent: Sep. 13, 2016

(54) VENTRICULAR ASSIST BLOOD PUMP

(75) Inventors: Takayuki Miyakoshi, Nagano (JP); Shinji Kobayashi, Nagano (JP); Hideki Kanebako, Nagano (JP); Tomoya Kitano, Nagano (JP)

(73) Assignee: SUN MEDICAL TECHNOLOGY RESEARCH CORPORATION, Nagano (JP)

( * ) Notice: Subject to any disclaimer, the term of this patent is extended or adjusted under 35 U.S.C. 154(b) by 0 days.

(21) Appl. No.: 14/388,264

(22) PCT Filed: Mar. 27, 2012

(86) PCT No.: PCT/JP2012/057999
§ 371 (c)(1),
(2), (4) Date: Sep. 26, 2014

(87) PCT Pub. No.: WO2013/145134
PCT Pub. Date: Oct. 3, 2013

(65) Prior Publication Data
US 2015/0297812 A1    Oct. 22, 2015

(51) Int. Cl.
*A61N 1/362*    (2006.01)
*A61M 1/10*    (2006.01)
*A61M 1/12*    (2006.01)

(52) U.S. Cl.
CPC ........... *A61M 1/1005* (2014.02); *A61M 1/101* (2013.01); *A61M 1/122* (2014.02); *A61M 1/1086* (2013.01); *A61M 2205/3334* (2013.01)

(58) Field of Classification Search
CPC .. A61M 1/1005; A61M 1/122; A61M 1/101; A61M 1/1086; A61M 2205/3334
See application file for complete search history.

(56) References Cited

U.S. PATENT DOCUMENTS 6,572,530 B1    6/2003  Araki et al.
8,226,712 B1    7/2012  Frazier et al.
8,512,013 B2 *  8/2013  LaRose ................. A61M 1/101
                                                    415/900

(Continued)

FOREIGN PATENT DOCUMENTS

CN    1278188 A      12/2000
CN    101927038 A    12/2010

(Continued)

OTHER PUBLICATIONS

International Search Report mailed Jul. 3, 2012 in International Application No. PCT/JP2012/057999.
LaRose, Jeffrey A. et al. "Design Concepts and Principle of Operation of the HeartWare Ventricular Assist System." American Society of Artificial Internal Organs Journal, 2010, vol. 56, No. 4, p. 285-289.
Sun Medical Technology Research Corporation, "Uekomi-gata Hojo Jinko Shinzo Evaheart, Nov. 2011".

(Continued)

*Primary Examiner* — Robert N Wieland
(74) *Attorney, Agent, or Firm* — Hauptman Ham, LLP

(57) ABSTRACT

A ventricular assist blood pump of the present invention includes: a rotational part having an impeller; and a housing which houses the rotational part therein. In the ventricular assist blood pump, a difference between a maximum flow rate and a minimum flow rate of a liquid in a state where the ventricular assist blood pump is connected to a liquid-discharge source which discharges the liquid while increasing and decreasing the flow rate of the liquid at a fixed cycle is 40% or more of a difference between the maximum flow rate and the minimum flow rate of the liquid in a state where the ventricular assist blood pump is not connected to the liquid-discharge source. A ventricular assist blood pump of the present invention can suppress the degree at which the health of a user deteriorates during long-term use compared to a conventional ventricular assist blood pump.

12 Claims, 5 Drawing Sheets

(56) References Cited

U.S. PATENT DOCUMENTS

| | | | |
|---|---|---|---|
| 2005/0084399 A1 | 4/2005 | Wampler et al. | |
| 2005/0107657 A1 | 5/2005 | Carrier et al. | |
| 2005/0267322 A1 | 12/2005 | Larose | |
| 2007/0142923 A1 | 6/2007 | Ayre et al. | |
| 2007/0238915 A1 | 10/2007 | Woodard | |
| 2007/0280841 A1* | 12/2007 | LaRose ................ | A61M 1/101 417/423.12 |
| 2007/0282298 A1 | 12/2007 | Mason | |
| 2011/0112354 A1 | 5/2011 | Nishimura et al. | |
| 2012/0078030 A1 | 3/2012 | Bourque | |
| 2012/0277520 A1 | 11/2012 | Duncan | |

FOREIGN PATENT DOCUMENTS

| | | |
|---|---|---|
| JP | 200558617 A | 3/2005 |
| JP | 2009523488 A | 6/2009 |
| JP | 2009297174 A | 12/2009 |
| WO | 99/12587 A1 | 3/1999 |
| WO | 2007084339 A2 | 7/2007 |

OTHER PUBLICATIONS

International Search Report in PCT/JP2012/058000, mailed Jul. 3, 2012.

Cheng et al., "Comparison of continuous-flow and pulsatile-flow left ventricular assist devices: is there an advantage to pulsatility?" Ann Cardiothorac Surg. Nov. 2014, pp. 573-581, vol. 3, No. 6, AME Publishing Company.

Soucy et al., "Rotary pumps and diminished pulsatility:do we need a pulse?", ASAIO Journal 2013, Jul.-Aug.; 59(4), pp. 355-366.

Soucy et al., "Defining pulsatility during continuous-flow ventricular assist devise support", The Journal of Heart and Lung Transplantation, Jun. 2013, vol. 32, No. 6, pp. 581-587.

Gao et al., "A pulsatile control algorithm of continuous-flow pump for heart recovery", ASAIO Journal 2012, Jul.-Aug.; 58(4), pp. 343-352.

Hajime Tsujiguchi, "Experimental Study on the Usefulness of Pulsatile Flow Extracorporeal Circulation", Kanazawa University Juzen Medical Society, Aug. 20, 1989, pp. 810-823, vol. 98, No. 4, Japan.

* cited by examiner

US 9,440,012 B2

VENTRICULAR ASSIST BLOOD PUMP

RELATED APPLICATIONS

The present application is a National Phase of International Application Number PCT/JP2012/057999, filed Mar. 27, 2012.

TECHNICAL FIELD

The present invention relates to a ventricular assist blood pump.

BACKGROUND ART

Conventionally, there have been known a ventricular assist blood pump which includes: a rotational part having an impeller; and housing which houses the rotational part therein (see patent literature 1 and non-patent literature 1, for example).

FIG. 6 is an exploded perspective view of a conventional ventricular assist blood pump 900. As shown in FIG. 6, the ventricular assist blood pump 900 includes: a rotational part 910 having an impeller 912; and housings 920, 922 which house the rotational part 910 therein. Such a conventional ventricular assist blood pump 900 can assist an action of a heart of a patient having cardiopathy during a period till he receives a heart transplant.

PRIOR ART LITERATURE

Patent Literature

Patent literature 1: JP-A-2009-5713488
Non-patent literature 1: Jeffrey A LaRose and three others, "American Society of Artificial Internal Organs journal", 2010, Vol. 56, No. 4, p. 285-289

SUMMARY OF THE INVENTION

Task to be Solved by the Invention

Cardiopathy is a disease which is very difficult to cure. At present, in many cases, only way to fundamentally cure such cardiopathy is with a heart transplant. However, it is a rare case where conditions necessary for carrying out the heart transplant (for example, the appearance of a donor who is compatible with a patient) are met readily. That is, under current circumstances, a patient waiting for a heart transplant (heart transplant waiting patient) has to wait for a donor who is compatible with the patient for a long period. Accordingly, there may be a case where a period until a heart transplant is carried out is extremely prolonged so that a patient cannot have a heart transplant eternally. In view of such circumstances, there has been proposed an idea that a patient continues the use of a ventricular assist system until he passes away without receiving a heart transplant.

As described above, there is a tendency that a period where a user of a ventricular assist blood pump (hereinafter simply referred to as "user") uses the ventricular assist blood pump is becoming longer than a period which has been conventionally estimated. Accordingly, the importance of suppressing the degree at which the health of a user deteriorates during a long-term use is steadily increasing.

Accordingly, it is an object of the present invention to provide a ventricular assist blood pump which can suppress the degree at which the health of a user deteriorates during long-term use compared to a conventional ventricular assist blood pump.

Means for Solving the Task

Inventors of the present invention have come up with an idea that the pulsatility of a blood flow discharged from a ventricular assist blood pump is an important factor to be taken into consideration in suppressing the degree at which the health of a user deteriorates, and the present invention has been made under such finding. That is, a ventricular assist blood pump provided with a rotation part rotates a rotation part at a fixed rotational speed and hence, the ventricular assist blood pump essentially produces a blood flow having no pulsatility. However, a heart moves blood by expansion and contraction (beat) of muscles thereof and hence, from a viewpoint of the health of a user, it is preferable that the blood flow has pulsatility. The present invention relates to a ventricular assist blood pump which can make use of pulsatility of a blood flow generated by heart beat while provided with a rotation part. The ventricular assist blood pump according to the present invention has the following constitution.

(1) A ventricular assist blood pump of the present invention includes: a rotational part having an impeller; and a housing which houses the rotational part therein, and is characterized in that a difference between a maximum flow rate and a minimum flow rate of the liquid in a state where the ventricular assist blood pump is connected to a liquid-discharge source which discharges while increasing and decreasing the flow rate of the liquid at a fixed cycle is 40% or more of a difference between the maximum flow rate and the minimum flow rate of the liquid in a state where the ventricular assist blood pump is not connected to the liquid-discharge source.

According to the ventricular assist blood pump of the present invention, a difference between the maximum flow rate and the minimum flow rate of the liquid in a state where the ventricular assist blood pump is connected to the liquid-discharge source is 40% or more of a difference between the maximum flow rate and the minimum flow rate of the liquid in a state where the ventricular assist blood pump is not connected to the liquid discharge source and hence, a change in flow rate is sufficiently large with respect to a change in head. As a result, compared to the conventional ventricular assist blood pump, it is possible to suppress the degree at which the health of a user deteriorates during long-term use.

In view of the above, it is preferable that a difference between the maximum flow rate and the minimum flow rate of the liquid discharged from the ventricular assist blood pump is 60% or more of a difference between the maximum flow rate and the minimum flow rate of the liquid in a state where the ventricular assist blood pump is not connected to the liquid-discharge source, and it is more preferable that the percentage is 80% or more. Further, it is needless to say that 100% is the most preferable as an ideal percentage.

"liquid-discharge source" is a heart when a ventricular assist blood pump is actually used in a body and is a device simulating an action of the heart when the ventricular assist blood pump is tested outside the body.

"difference between a maximum flow rate and a minimum flow rate of the liquid in a state where the ventricular assist blood pump is connected" is not calculated based on a flow rate of the liquid obtained when only the ventricular assist blood pump is taken into account (so-called pump flow) but is calculated based on a flow rate obtained when the whole system including the liquid-discharge source, the ventricular assist blood pump and the like is taken into account (so-called total flow).

In this specification, "ventricular assist blood pump" is a main element of the ventricular assist system, and is a pump which assists a heart weakened by a disease by applying a moving force to blood.

"ventricular assist system" is a set of devices which is used in the form that the system is mounted on the heart weakened by a disease, and a system which mainly assists the movement of blood.

It is preferable that the ventricular assist blood pump of the present invention is an embedded-type ventricular assist blood pump which is used in an embedded manner in a body in an actual use (that is, the ventricular assist blood pump being so small that the ventricular assist blood pump can be used in an embedded manner in a body).

(2) A ventricular assist blood pump of the present invention includes: a rotational part having an impeller and a housing which houses the rotational part therein, and is characterized in that a relationship between a head and a flow rate is measured using a liquid whose viscosity and density correspond to viscosity and density of blood as a working liquid, and in a graph where the head is taken on an axis of ordinates using mmHg as a unit and the flow rate is taken on an axis of abscissas using L/min as a unit, the flow rate is set to 5 L/min or more at a point where the head is lower than a shutoff head by 20 mmHg in pressure at a fixed rotational speed.

According to the ventricular assist blood pump of the present invention, the flow rate is set to 5 L/min or more at a point where the head is lower than a shutoff head by 20 mmHg in pressure and hence, the flow rate becomes sufficiently large with respect to a magnitude of the head compared to a conventional ventricular assist blood pump whereby the pulsatility of blood flow generated by heart beat can be sufficiently made use of. As a result, compared to the conventional ventricular assist blood pump, the ventricular assist blood pump of the present invention can suppress the degree at which the health of a user deteriorates during long-term use.

In view of the above, it is preferable that the flow rate is set to 8 L/min or more at a point where the head is lower than a shutoff head by 20 mmHg in pressure, and it is more preferable that the flow rate is set to 10 L/min or more at a point where the head is lower than a shutoff head by 20 mmHg in pressure.

The "shutoff head" indicates a head when a flow rate is 0 L/min.

(3) A ventricular assist blood pump of the present invention includes: a rotational part having an impeller and a housing which houses the rotational part therein, and is characterized in that a relationship between a head and a flow rate is measured using a liquid whose viscosity and density correspond to viscosity and density of blood as a working liquid, and in a graph where the head is taken on an axis of ordinates using mmHg as a unit and the flow rate is taken on an axis of abscissas using L/min as a unit, the inclination of the graph is set to a value which falls within a range of −5 to 0 at a point where the head is set to 100 mmHg and the flow rate is set to 5 L/min at a fixed rotational speed.

According to the ventricular assist blood pump of the present invention, under the above-mentioned condition, the inclination of the graph is set to a value which falls within a range of −5 to 0 at a point where the head is set to 100 mmHg and the flow rate is set to 5 L/min. Accordingly, a change in flow rate becomes sufficiently large with respect to a change in head compared to a conventional ventricular assist blood pump and hence, the pulsatility of blood flow generated by heart beat can be sufficiently made use of. As a result, compared to the conventional ventricular assist blood pump, the ventricular assist blood pump of the present invention can suppress the degree at which the health of a user deteriorates during long-term use.

The reason why the inclination of the graph is set to a value which falls within a range of −5 to 0 is as follows. That is, when the inclination of the graph is less than −5, it is difficult to make a change in flow rate sufficiently large with respect to a change in head, while when the inclination of the graph is more than 0, although the head is increased, the flow rate is also increased and hence, the value is not a significant value. In view of the above, it is preferable that the inclination of the graph is set to a value which falls within a range of −4 to 0, and it is more preferable that the inclination of the graph is set to a value which falls within a range of −3 to 0.

(4) A ventricular assist blood pump of the present invention includes: a rotational part having an impeller and a housing which houses the rotational part therein, and is characterized in that a change in flow rate is large with respect to a change in head when the liquid is made to flow in the ventricular assist blood pump with a rotational speed of the rotational part set to a fixed value.

Due to such a constitution, according to the ventricular assist blood pump of the present invention, since a change in flow rate is large with respect to a change in head (that is, a change in pressure generated by heart beat), the ventricular assist blood pump of the present invention can sufficiently make use of the pulsatility of the blood flow generated by heart beat. Accordingly, compared to the conventional ventricular assist blood pump, the ventricular assist blood pump of the present invention can suppress the degree at which the health of a user deteriorates during long-term use.

"with a rotational speed of the rotational part set to a fixed value" does not means that a rotational speed of the rotational part should be absolutely set to a fixed value but means that the rotational speed is set to a fixed value when there is no change in head.

(5) According to the ventricular assist blood pump of the present invention, a liquid whose viscosity and density correspond to viscosity and density of blood is used as a working liquid, and when a pressure loss is measured in a state where the ventricular assist blood pump is stopped and the flow rate is set to 6 L/min, the pressure loss is 20 mmHg or less.

Due to such a constitution, the ventricular assist blood pump of the present invention can sufficiently make use of the pulsatility of the blood flow by making a pressure loss sufficiently low.

It is more preferable that the pressure loss of the ventricular assist blood pump falls within a range of 5 mmHg to 16 mmHg. The reason is as follows. When the pressure loss is larger than 16 mmHg, there may be a case where it is difficult to make use of the pulsatility of the blood flow by making the pressure loss sufficiently low. On the other hand, when the pressure loss is less than 5 mmHg, there may be a case where a force to move blood cannot be sufficiently ensured due to a problem on designing the rotational part.

In this specification, "pressure loss of the ventricular assist blood pump" means a pressure necessary for a working liquid to pass through the ventricular assist blood pump when the working liquid is made to flow at a predetermined flow rate (6 L/min) in a state the ventricular assist blood pump is stopped.

(6) According to the ventricular assist blood pump of the present invention, a numerical value obtained by dividing a volume of the rotational part by a capacity of the housing falls within a range of 0.01 to 0.50.

Due to such a constitution, the ventricular assist blood pump of the present invention can sufficiently make use of the pulsatility of the blood flow by making pressure loss low enough and hence, the rotational part can sufficiently ensure a force for moving blood.

The reason why the numerical value obtained by dividing a volume of the rotational part by a capacity of the housing falls within a range of 0.01 to 0.50 is as follows. That is, when the value is more than 0.50, the volume of the rotational part becomes so large that there may be a case where it is difficult to sufficiently make use of the pulsatility of the blood flow by making the pressure loss sufficiently low. On the other hand, when the value is less than 0.01, there may be a case where a force to move blood cannot be sufficiently ensured.

In view of the above, it is preferable that the numerical value obtained by dividing a volume of the rotational part by a capacity of the housing falls within a range of 0.06 to 0.12.

In this specification, "capacity of the housing" does not mean only a capacity of a portion of the housing where the impeller is stored (a so-called storing part or pump chamber) but means a capacity of the whole housing including a capacity of a portion where blood is introduced into the ventricular assist blood pump (a portion connectable with or separable from the introduction-side artificial vessel ("artificial vessel" includes, in its category, both a flexible artificial vessel made of fabric or a soft resin, and a pipe-shaped artificial vessel made of a hard resin or metal. The same hereinafter)) and a capacity of a portion where blood is discharged (a portion connectable with and separable from the delivery-side artificial vessel).

(7) According to the ventricular assist blood pump of the present invention, a minimum cap between the impeller and an inner wall of the housing during the operation of the ventricular assist blood pump falls within a range of 0.1 mm to 2.0 mm.

Due to such a constitution, the ventricular assist blood pump of the present invention can sufficiently make use of the pulsatility of the blood flow by making a pressure loss low enough and hence, the impeller can sufficiently ensure a force for moving blood.

The reason why the minimum gap between the impeller and the inner wall of the housing during the operation of the ventricular assist blood pump falls within a range of 0.1 mm to 2.0 mm is as follows. That is, when the minimum gap is less than 0.1 mm, a space between the impeller and the housing becomes so short that there may be a case where it is difficult to sufficiently make use of the pulsatility of the blood flow by making the pressure loss sufficiently low. On the other hand, when the minimum gap is more than 2.0 mm, there may be a case where a force to move blood cannot be sufficiently ensured.

When the minimum gap between an outer end of the impeller and an inner wall of the housing is more than 0.1 mm, interruption of rotation of the impeller resulting from a foreign object (thrombus, for example) which is caught in between the impeller and the housing can be suppressed. As a result, it is possible to provide a ventricular assist blood pump with high stability of operation.

In view of the above, it is more preferable that the minimum gap between the impeller and the inner wall of the housing falls within a range of 0.5 mm to 0.8 mm.

(8) According to the ventricular assist blood pump of the present invention, the ventricular assist blood pump is formed of a centrifugal-type ventricular assist blood pump, and a numerical value obtained by dividing a minimum inner diameter of a blood introducing portion of the ventricular assist blood pump by a diameter of rotation of the impeller may preferably be set to a value which falls within a range of 0.2 to 0.8.

Due to such a constitution, the ventricular assist blood pump of the present invention can make use of the pulsatility of the blood flow by making the pressure loss sufficiently low, and it is possible to provide a sufficiently compact ventricular assist blood pump.

The reason why the numerical value obtained by dividing the minimum inner diameter of the blood introducing portion of the ventricular assist blood pump by the diameter of rotation of the impeller is set to a value which falls within a range of 0.2 to 0.8 is as follows. That is, when the value is less than 0.2, the minimum inner diameter becomes so small that there may be a case where it is difficult to sufficiently make use of the pulsatility of the blood flow by making the pressure loss sufficiently low. On the other hand, when the value is more than 0.8, it is difficult to provide a sufficiently compact ventricular assist blood pump.

(9) According to the ventricular assist blood pump of the present invention, the ventricular assist blood pump is formed of a centrifugal-type ventricular assist blood pump, and a numerical value obtained by dividing the minimum inner diameter of a blood delivering portion of the ventricular assist blood pump by a diameter of rotation of the impeller is set to a value which may preferably fall within a range of 0.2 to 0.8.

Due to such a constitution, the ventricular assist blood pump of the present invention can make use of the pulsatility of the blood flow by making the pressure loss sufficiently low, and it is possible to provide a sufficiently compact ventricular assist blood pump.

The reason why the numerical value obtained by dividing the minimum inner diameter of the blood delivering portion of the ventricular assist blood pump by the diameter of rotation of the impeller is set to a value which falls within a range of 0.2 to 0.8 is as follows. That is, when the value is less than 0.2, the minimum inner diameter becomes so small that there may be a case where it is difficult to sufficiently make use of the pulsatility of the blood flow by making the pressure loss sufficiently low. On the other hand, when the value is more than 0.8, it is difficult to provide a sufficiently compact ventricular assist blood pump.

BRIEF DESCRIPTIONS OF THE DRAWINGS

FIG. 1 is a view for explaining a ventricular assist blood pump 110 according to an embodiment when the ventricular assist blood pump 110 is actually used.

FIG. 2(a), FIG. 2(b) and FIG. 2(c) are views for explaining a ventricular assist blood pump 110 according to the embodiment.

FIG. 3(a), FIG. 3(b) and FIG. 3(c) are views for explaining a rotational part 10 in the embodiment.

FIG. 4(a) and FIG. 4(b) are graphs for explaining a mode of a blood flow which is measured by using the ventricular assist blood pump 110 and a liquid discharge source according to the embodiment.

BEST MODE FOR CARRYING OUT THE INVENTION

Hereinafter, a ventricular assist blood pump of the present invention is explained based on an embodiment shown in drawings.

[Embodiment]

Figure 1:
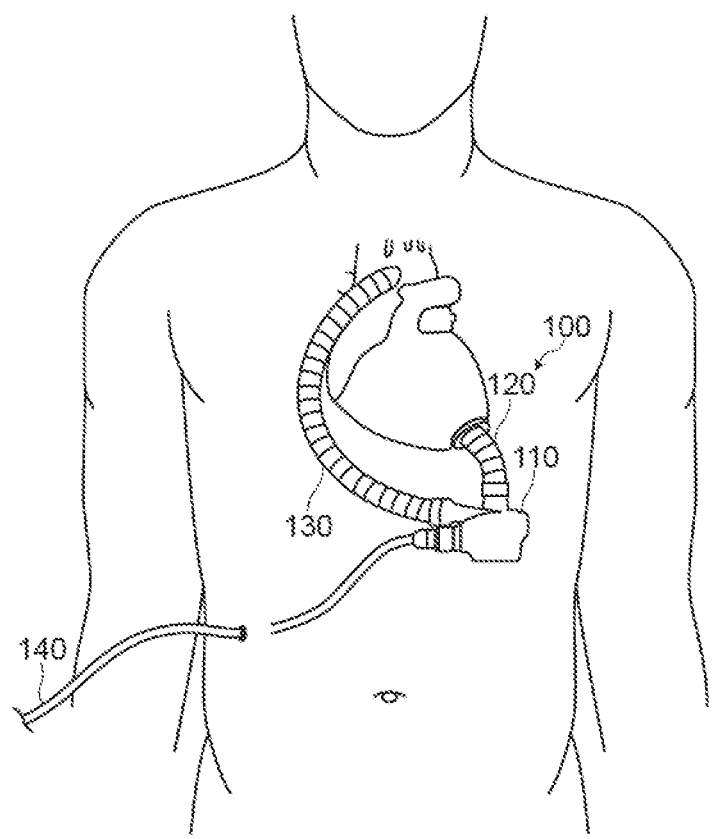

FIG. 1 is a view for explaining a ventricular assist blood pump 110 according to an embodiment when the ventricular assist blood pump 110 is actually used.

Figure 2A:
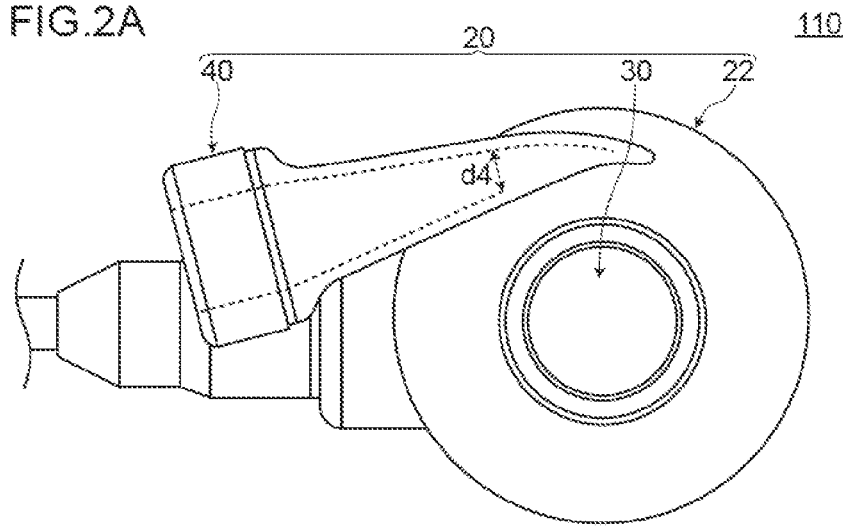
Figure 2B:
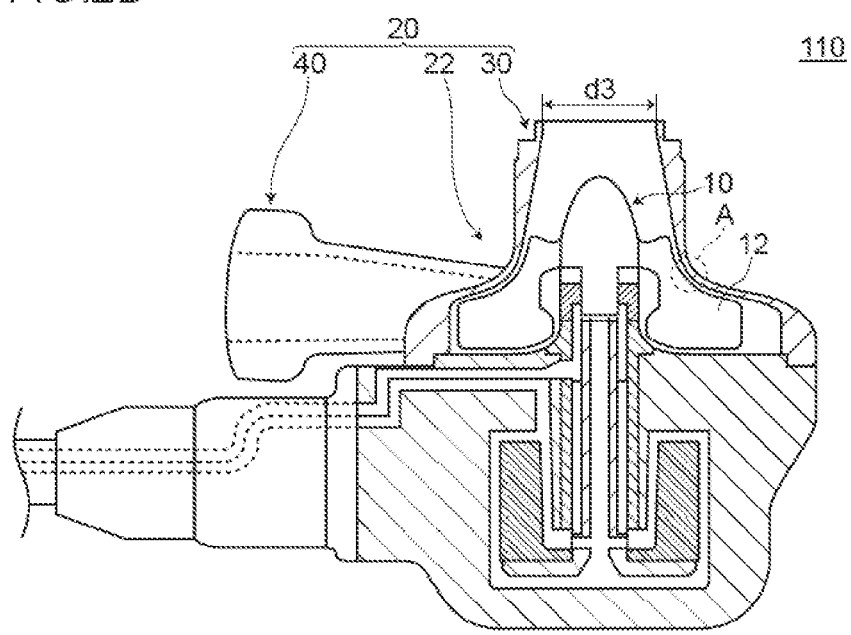
Figure 2C:
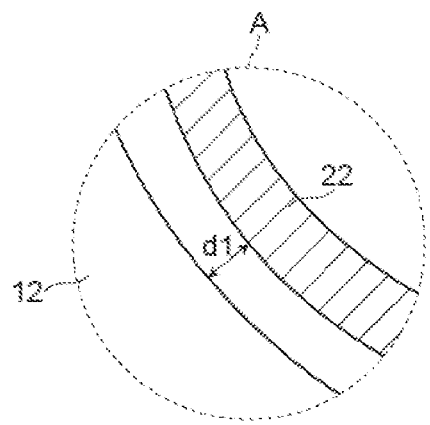

FIG. 2(a), FIG. 2(b) and FIG. 2(c) are views for explaining a ventricular assist blood pump 110 according to the embodiment. FIG. 2(a) is a top plan view of the ventricular assist pump 110, FIG. 2(b) is a cross-sectional view of the ventricular assist pump 110, and FIG. 2(c) is an enlarged view of an area that indicated a sign A in FIG. 2(b).

Figure 3A:
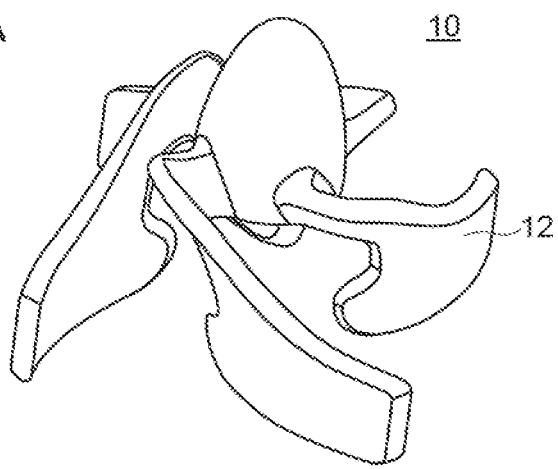
Figure 3B:
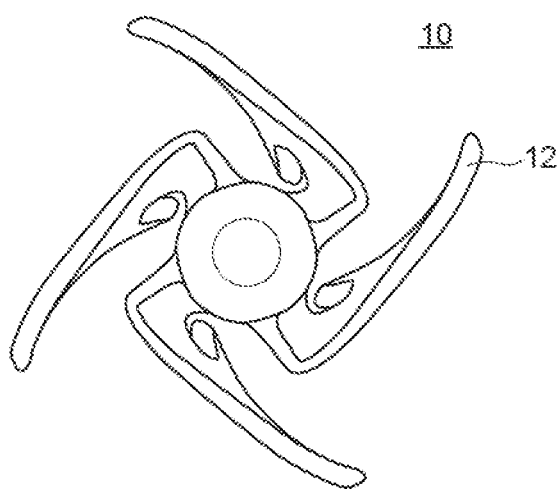
Figure 3C:
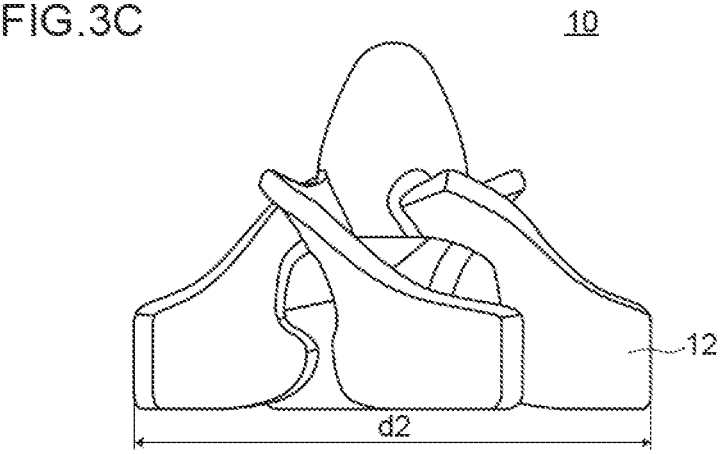

FIG. 3(a), FIG. 3(b) and FIG. 3(c) are views for explaining a rotational part 10 in the embodiment. FIG. 3(a) is a perspective view of the rotational part 10, FIG. 3(b) is a top plan view of the rotational part 10, and FIG. 3(c) is a front view of the rotational part 10.

Figure 4A:
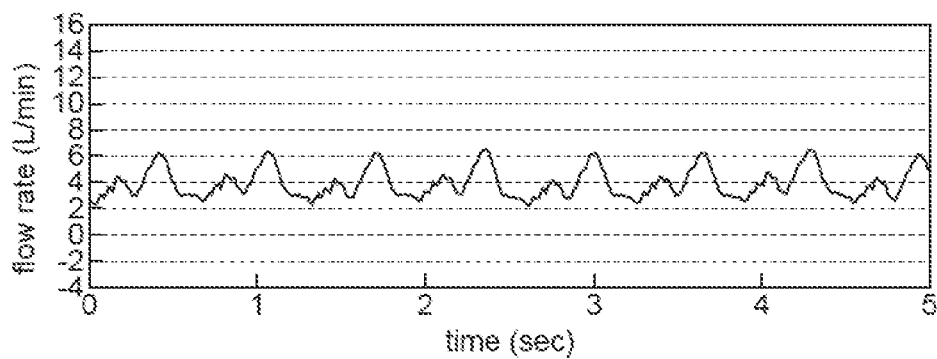
Figure 4B:
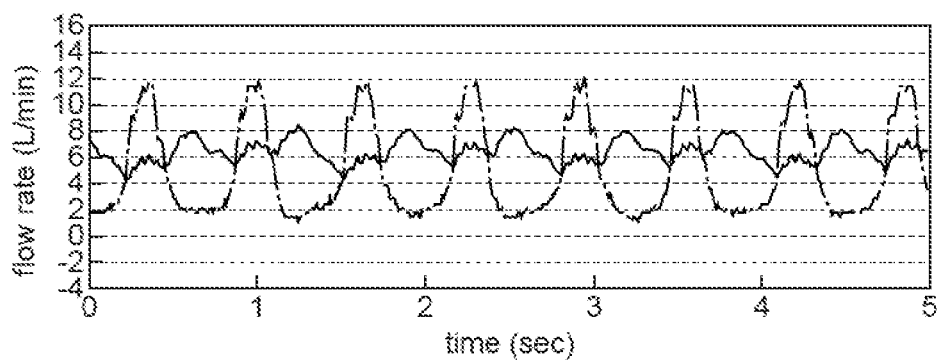

FIG. 4(a) and FIG. 4(b) are graphs for explaining a mode of a blood flow which is measured by using the ventricular assist blood pump 110 and a liquid discharge source according to the embodiment. FIG. 4(a) is a graph showing a mode of blood flow in a state where the ventricular assist blood pump 110 is not connected to a device which simulates a patient's heart suffering a functional disorder (beat simulator), and FIG. 4(b) is a graph showing a mode of the blood flow in a state where the ventricular assist blood pump 110 is connected to the device. In FIG. 4(a) and FIG. 4(b), a flow rate (L/min) is taken on an axis of ordinates, and time (sec) is taken on an axis of abscissas. In the graphs in FIG. 4(a) and FIG. 4(b), a solid line indicates a flow rate of a liquid when the whole system including a liquid discharge source, the ventricular assist blood pump and the like (total flow) is taken into consideration, and a chain line indicates a flow rate when only the ventricular assist blood pump is taken into consideration (pump flow).

Figure 5:
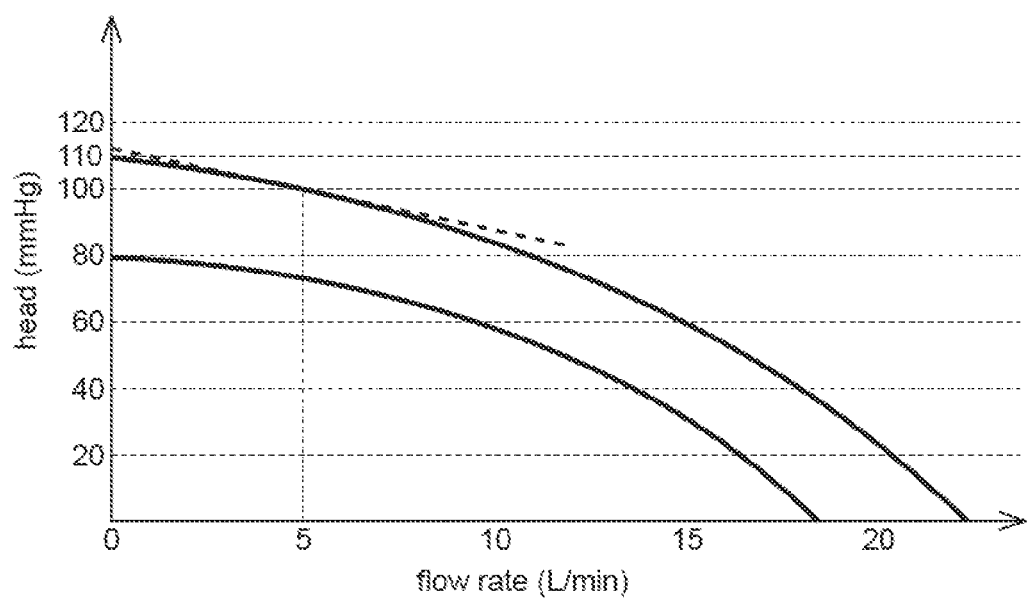
FIG. 5 is a graph for explaining a relationship between a head and a flow rate of the ventricular assist blood pump 110 according to the embodiment.
Figure 6:
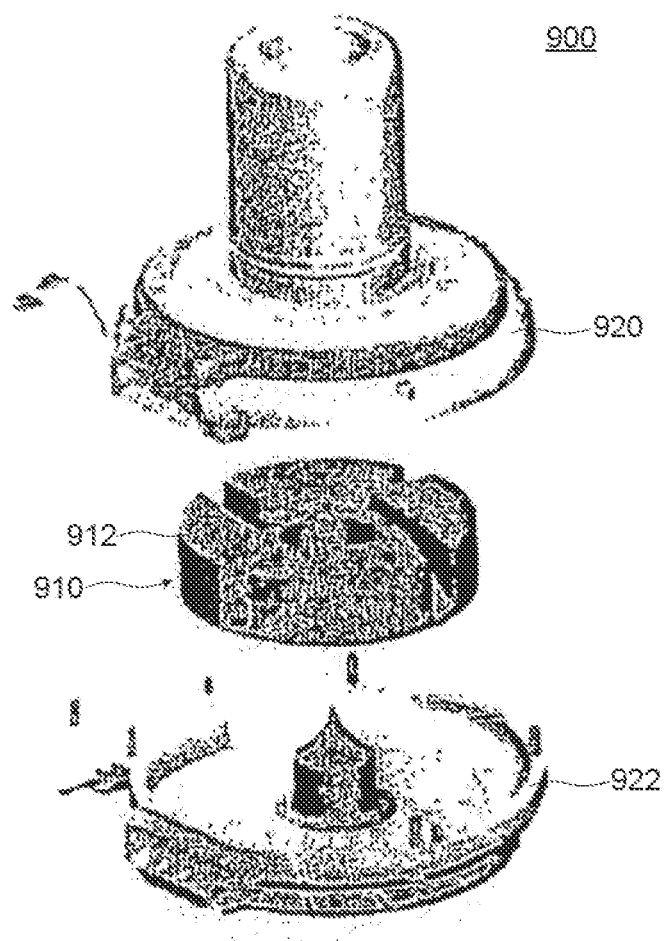
FIG. 6 is an exploded perspective view of a conventional ventricular assist blood pump 900.

FIG. 5 is a graph for explaining a relationship between a head and a flow rate of the ventricular assist blood pump 110 according to the embodiment. The upper graph is a graph where a flow rate is set to 5 L/min when a head is 100 mmHg, and the lower graph is a graph where a shutoff head is set to 80 mmHg. A broken line which is in contact with the upper graph is a tangent at a point where the head is 100 mmHg and the flow rate is 5 L/min.

As shown in FIG. 1, the ventricular assist blood pump 110 is a part of the ventricular assist system 100. The ventricular assist system 100 includes: the ventricular assist blood pump 110; an introduction-side artificial vessel 120; a delivery-side artificial vessel 130; a cable 140; and a control part 150 (not shown in the drawing). The control part 150 is connected to the ventricular assist blood pump 110 by way of the cable 140 and controls the operation of the ventricular assist blood pump 110.

As shown in FIG. 2(a), FIG. 2(b) and FIG. 2(c), the ventricular assist blood pump 110 is a centrifugal-type ventricular assist blood pump which includes: a rotational part 10 having an impeller 12 (see FIG. 3(a), FIG. 3(b) and FIG. 3(c)); and a housing 20 which houses the rotational part 10 therein. The ventricular assist blood pump 110 is an embedded type ventricular assist blood pump which is used in a state where the ventricular assist blood pump 110 is embedded in a human body in an actual use. The ventricular assist blood pump 110 further includes, in addition to the constitutional elements described above, a drive part which rotatably drives the rotational part 10, a flow path for a cool sealing liquid (also referred to as a purge liquid, water or saline, for example) which performs functions such as lubrication, cooling and maintaining of a sealing capacity of the inside of the ventricular assist blood pump 110 and the like. However, these constitutional elements are not directly related to the present invention and hence, the explanation of these constitutional elements and the description of symbols in the drawings are omitted.

The housing 20 includes: a storing part 22 which stores the rotational part; a blood introducing portion 30 which introduces blood into the ventricular assist blood pump 110 from the outside of the ventricular assist blood pump 110; and a blood delivering portion 40 which discharges the blood to the outside of the ventricular assist blood pump 110 (aorta) from the inside of the ventricular assist blood pump 110. The blood introducing portion 30 is connected to an introduction-side artificial vessel 120, and the blood delivering portion 40 is connected to a delivery-side artificial vessel 130. The blood introducing portion and the blood delivering portion may be formed separately from the housing.

In the ventricular assist blood pump 100, when a liquid (blood in actual use in a body) is made to flow in the ventricular assist blood pump 110 with a rotational speed of the rotational part 10 set to a fixed value, a change in flow rate is large with respect to a change in head.

A method of obtaining a graph shown in FIG. 4(a) and a graph shown in FIG. 4(b) is explained. The graphs shown in FIG. 4(a) and FIG. 4(b) are obtained by the following method. That is, a ventricular assist blood pump similar to the ventricular assist blood pump 110 according to the embodiment is actually manufactured, an experiment is performed by connecting the ventricular assist blood pump to a beat simulator which simulates the delivery of blood from a heart (beat simulator), and the result of the experiment is made into graphs. As a working liquid served for the test, a glycerin aqueous solution whose viscosity is prepared to 3.5 cP for example, is used. The result of graphs (waveforms) reflects disturbance factors such as a pressure spike waveform generated by opening or closing a valve.

As shown in FIG. 4(a), a difference between the maximum flow rate (average maximum flow rate being 6.29 L/min) and the minimum flow rate (average minimum flow rate being 2.45 L/min) of a liquid in a state where the ventricular assist blood pump 110 is not connected to the liquid-discharge source is 3.84 L/min. On the other hand, as shown in FIG. 4(b), a difference between a maximum flow rate (average maximum flow rate being 8.25 L/min) and a minimum flow rate (average minimum flow rate being 4.91 L/min) of a liquid in a state where the ventricular assist blood pump 110 is connected to the liquid-discharge source is 3.34 L/min. Accordingly, in the ventricular assist blood pump 110, the difference between the maximum flow rate and the minimum flow rate of the liquid in a state where the ventricular assist blood pump 110 is connected to the liquid-discharge source which delivers the liquid while increasing and decreasing the flow rate of the liquid at a fixed cycle is 40% or more of the difference between the maximum flow rate and the minimum flow rate of the liquid in a state where the ventricular assist blood pump 110 is not connected to the liquid-discharge source. In the ventricular assist blood pump 110, the percentage is 80% or more. To be specific, the difference between the maximum flow rate and the minimum flow rate of the liquid in a state where the ventricular assist blood pump 110 is connected to the liquid-discharge source which delivers the liquid while increasing and decreasing the flow rate of the liquid at a fixed cycle is approximately 87% of the difference between the maximum flow rate and the minimum flow rate of the liquid in a state where the ventricular assist blood pump 110 is not connected to the liquid-discharge source.

As shown in FIG. 4(b), a difference between a maximum flow rate (average maximum flow rate being 11.73 L/min) and a minimum flow rate (average minimum flow rate being 1.38 L/min) of a pump flow rate in a state where the ventricular assist blood pump 110 is connected to liquid-discharge source is 10.35 L/min. Accordingly, in the ventricular assist blood pump 110, the difference between the maximum flow rate and the minimum flow rate of the pump flow rate in a state where the ventricular assist blood pump 110 is connected to the liquid-discharge source which discharges the liquid while increasing and decreasing the flow rate of the liquid at a fixed cycle is 200% or more of a difference between the maximum flow rate and the minimum flow rate of the liquid in a state where the ventricular assist blood pump 110 is not connected to the liquid-discharge source. In the ventricular assist blood pump 100, the percentage is 250% or more. To be specific, the difference between the maximum flow rate and the minimum flow rate of the pump flow rate in a state where the ventricular assist blood pump 110 is connected to liquid-discharge source is approximately 270 % of the difference between the maximum flow rate and the minimum flow rate of the liquid in a state where the ventricular assist blood pump 110 is not connected to the liquid-discharge source.

As described above, the ventricular assist blood pump 110 where the difference between the maximum flow rate and the minimum flow rate of the pump flow rate in a state where the ventricular assist blood pump is connected to the liquid-discharge source which discharges the liquid while increasing and decreasing the flow rate of the liquid at a fixed cycle is 200% or more of the difference between the maximum flow rate and the minimum flow rate of the liquid in a state where the ventricular assist blood pump is not connected to the liquid-discharge source. Accordingly, a change in flow rate becomes sufficiently large with respect to a change in head. As a result, compared to the conventional ventricular assist blood pump, the ventricular assist blood pump 110 can suppress the degree at which the health of a user deteriorates during long-term use.

A method of obtaining the graph in FIG. 5 is explained. The graph in FIG. 5 is obtained by the following method. That is, a ventricular assist blood pump similar to the ventricular assist blood pump 110 according to the embodiment is manufactured, an experiment is performed using the ventricular assist blood pump, and the result of the experiment is made into a graph. As a working liquid served for the test, a glycerin aqueous solution whose viscosity of is set to 3.5 cP is used.

In the ventricular assist blood pump 110, as shown in FIG. 5, a relationship between a head and a flow rate is measured using a liquid whose viscosity and density correspond to viscosity and density of blood as a working liquid, and when a graph is prepared by taking the head on an axis of ordinates using mmHg as a unit and the flow rate on an axis of abscissas using L/min as a unit at a fixed rotational speed, the flow rate is set to 5 L/min or more at a point where the head is lower than a shutoff head by 20 mmHg, and more particularly is set to 10 L/min or more at such a point.

Further, in the ventricular assist blood pump 110, similarly as shown in FIG. 5, a relationship between a head and a flow rate is measured using a liquid whose viscosity and density correspond to viscosity and density of blood which constitutes a working liquid, and when a graph is prepared by taking the head on an axis of ordinates using mmHg as a unit and the flow rate on an axis of abscissas using L/min as a unit at a fixed rotational speed, the inclination of the graph at a point where the head is 100 mHg and the flow rate is 5 L/min falls within a range of −5 to 0, more particularly −3 to 0. To be specific, the inclination of the graph is approximately −2.4.

In the ventricular assist blood pump 110, the rotational part 10 is directly connected to a drive part by way of a rotary shaft. A bearing portion of the rotational part 10 is a mechanical seal and is configured to prevent the intrusion of blood. In the ventricular assist blood pump 110, a minimum gap between the impeller 12 and an inner wall of the housing 20 during the operation of the ventricular assist blood pump 110 falls within a range of 0.1 mm to 2.0 mm, more preferably falls within a range of 0.5 mm to 0.8 mm. For example, the minimum gap is 0.6 mm. (see d1 in FIG. 2(c)).

In the ventricular assist blood pump 110, a liquid whose viscosity and density correspond to viscosity and density of blood is used as a working liquid. When the pressure loss is measured in a state where the ventricular assist blood pump 110 is stopped and the flow rate is set to 6 L/min, the pressure loss is 20 mmHg or less, more preferably falls within a range of 5 mmHg to 16 mmHg. For example, the pressure loss is 14 mmHg.

In the ventricular assist blood pump 110, a numerical value obtained by dividing a volume of the rotational part 10 by a capacity of the housing 20 falls within a range of 0.01 to 0.50, more preferably falls within a range of 0.06 to 0.12. For example, the numerical value is 0.09.

A diameter of rotation of the impeller 12 (see d2 in FIG. 3(c)) is 40 mm, and a minimum inner diameter of the blood introducing portion 30 of the ventricular assist blood pump 110 (see d3 in FIG. 2(b)) is 16 mm. Accordingly, a numerical value obtained by dividing the minimum inner diameter of the blood introducing portion 30 of the ventricular assist blood pump ventricular assist blood pump 110 by the diameter of rotation of the impeller 12 falls within a range of 0.2 to 0.8, and to be specific, the numerical value is 0.4.

The inner diameter of the blood introducing portion 30 becomes minimum in a connecting portion between the blood introducing portion 30 and the introduction-side artificial blood vessel 120 (end side of the blood introducing portion 30, see FIG. 2(b)). The minimum inner diameter is a diameter of such a portion.

Further, a minimum inner diameter of the blood delivering portion 40 of the ventricular assist blood pump 110 (see: d4 in FIG. 2(a)) is 10 mm. Accordingly, in the ventricular assist blood pump 110, a numerical value obtained by dividing the minimum inner diameter of the blood delivering portion 40 of the ventricular assist blood pump 110 by a diameter of rotation of the impeller 12 falls within a range of 0.2 to 0.8, and to be specific, the numerical value is 0.25. The inner diameter of the blood delivering portion 40 becomes minimum in the vicinity of a joint portion between the blood delivering portion 40 and the storing part 22 (back side of the blood delivering portion 40, see FIG. 2(b)). The minimum inner diameter is a diameter of such a portion.

Hereinafter, advantageous effects of the ventricular assist blood pump 110 according to the embodiment are explained.

According to the ventricular assist blood pump 110 of the embodiment, a difference between the maximum flow rate and the minimum flow rate of the liquid in a state where the ventricular assist blood pump 110 is connected to the liquid-discharge source is 40% or more of a difference between the maximum flow rate and the minimum flow rate of the liquid in a state where the ventricular assist blood pump 110 is not connected to the liquid-discharge source and hence, a change in flow rate is sufficiently large with respect to a change in head. As a result, compared to the conventional ventricular assist blood pump, it is possible to suppress the degree at which the health of a user deteriorates during long-term use.

According to the ventricular assist blood pump 110 of the embodiment, the flow rate is set to 5 L/min or more at a point where the head is lower than a shutoff head by 20 mmHg in pressure and hence, the flow rate becomes sufficiently large with respect to a magnitude of the head compared to a conventional ventricular assist blood pump whereby the pulsatility of blood flow generated by heart beat can be sufficiently made use of. As a result, compared to the conventional ventricular assist blood pump, the ventricular assist blood pump 110 of the present invention can suppress the degree at which the health of a user deteriorates during long-term use.

According to the ventricular assist blood pump 110 of the embodiment, the head is 100 mmHg and the inclination of the graph at a point were the flow rate is 5 L/min falls within a range of −5 to 0 and hence, a change in flow rate becomes sufficiently large with respect to a change in head compared to the conventional ventricular assist blood pump, and the pulsatility of blood flow generated by heart beat can be sufficiently made use of. As a result, compared to the conventional ventricular assist blood pump, it is possible to suppress the degree at which the health of a user deteriorates during long-term use.

According to the ventricular assist blood pump 110 of the embodiment, since a change in flow rate is large with respect to a change in head, the ventricular assist blood pump of the present invention can sufficiently make use of the pulsatility of the blood flow generated by heart beat. Accordingly, compared to the conventional ventricular assist blood pump, the ventricular assist blood pump 110 of the present invention can suppress the degree at which the health of a user deteriorates during long-term use.

According to the ventricular assist blood pump 110 of the embodiment, a liquid whose viscosity and density correspond to viscosity and density of blood is used as a working liquid, and when a pressure loss is measured in a state where the ventricular assist blood pump 110 is stopped and the flow rate is set to 6 L/min, the pressure loss is 20 mmHg or less. Accordingly, it is possible to make the pressure loss sufficiently low and to sufficiently make use of the pulsatility of the blood flow.

According to the ventricular assist blood pump 110 of the embodiment, a numerical value obtained by dividing a volume of the rotational part by a capacity of the housing falls within a range of 0.01 to 0.50. Accordingly, it is possible to sufficiently make use of the pulsatility of the blood flow by making a pressure loss low enough and hence, the rotational part can sufficiently ensure a force for moving blood.

According to the ventricular assist blood pump 110 of the embodiment, a minimum gap between the impeller and an inner wall of the housing during the operation of the ventricular assist blood pump falls within a range of 0.1 mm to 2.0 mm. Accordingly, it is possible to sufficiently make use of the pulsatility of the blood flow by making a pressure loss low enough and hence, the impeller can sufficiently ensure a force for moving blood.

According to the ventricular assist blood pump 110 of the embodiment, the ventricular assist blood pump 110 is formed of a centrifugal-type ventricular assist blood pump, and a numerical value obtained by dividing a minimum inner diameter of a blood introducing portion 30 of the ventricular assist blood pump 110 by a diameter of rotation of the impeller 12 is set to a value which fails within a range of 0.2 to 0.8. Accordingly, it is possible to make use of the pulsatility of the blood flow by making the pressure loss sufficiently low, and it is possible to provide a sufficiently compact ventricular assist blood pump.

According to the ventricular assist blood pump 110 of the embodiment, a numerical value obtained by dividing the minimum inner diameter of a blood delivering portion 40 of the ventricular assist blood pump 110 by a diameter of rotation of the impeller 12 is set to a value which falls within a range of 0.2 to 0.8. Accordingly, it is possible to make the pressure loss sufficiently low and to sufficiently make use of the pulsatility of the blood flow, and it is possible to make a sufficiently compact ventricular assist blood pump.

Although the present invention have been explained in conjunction with the above-described embodiment heretofore, the present invention is not limited to the above-mentioned embodiments, and the present invention can be carried out in various modes without departing from the gist of the present invention. For example, the following modifications can be considered.

(1) The sizes, the numbers, the materials and the shapes of the respective constitutional elements described in the above-mentioned embodiment are merely provided as examples, and can be changed without impairing the advantageous effects of the present invention.

(2) The ventricular assist blood pump 110 of the above-mentioned embodiment has the following four characteristics.

A difference between a maximum flow rate and a minimum flow rate of a liquid in a state where the ventricular assist blood pump is connected to the liquid-discharge source which delivers the liquid while increasing and decreasing the flow rate of the liquid at a fixed cycle is 40% or more of a difference between a maximum flow rate and a minimum flow rate of a liquid in a state where the ventricular assist blood pump is not connected to the liquid-discharge source.

A relationship between a head and a flow rate using a liquid whose viscosity and density correspond to viscosity and density of blood as a working liquid is measured, and when a graph is prepared by taking a head on an axis of ordinates using mmHg as a unit and a flow rate on an axis of abscissas using L/min as a unit at a fixed rotational speed, the flow rate is 5 L/min or more at a point where the head is lower than a shutoff head by 20 mmHg.

A relationship between a head and a flow rate is measured using a liquid whose viscosity and density correspond to viscosity and density of blood as a working liquid, and when a graph is prepared by taking a head on an axis of ordinates using mmHg as a unit and a flow rate on an axis of abscissas using L/min as a unit at a fixed rotational speed, the inclination of the graph at a point where the head is 100 mHg and the flow rate is 5 L/min falls within a range of −5 to 0.

When a liquid is made to flow with a rotational speed of the rotational part 10 set to a fixed value, a change in flow rate is large with respect to a change in head.

However, the present invention is not limited to a ventricular assist blood pump having these characteristics. Provided that a ventricular assist blood pump includes: a rotational part having an impeller; and a housing which houses the rotational part therein, and such a ventricular assist blood pump has any one of the above-mentioned four characteristics, the ventricular assist blood pump falls within the scope of the present invention.

REFERENCE SIGNS LIST

10: rotational part, 12: impeller, 20: housing, 22: storing part, 30: blood introducing portion, 40: blood delivering portion, 100: ventricular assist system, 110: ventricular assist blood pump, 120: introduction-side artificial vessel, 130: delivery-side artificial vessel, 140: cable

The invention claimed is:

1. A ventricular assist blood pump comprising:
a rotational part having an impeller and
a housing which houses the rotational part therein, wherein
a first numerical value obtained by dividing a volume of the rotational part by a capacity of the housing falls within a range of 0.01 to 0.50, and
a relationship between a head of the ventricular assist blood pump and a flow rate of the ventricular assist blood pump is measured using a liquid whose viscosity and density correspond to viscosity and density of blood as a working liquid, and in a graph where the head of the ventricular assist blood pump is taken on an axis of ordinates using mmHg as a unit and the flow rate of the ventricular assist blood pump is taken on an axis of abscissas using L/min as a unit, the flow rate of the ventricular assist blood pump is set to 5 L/min or more at a point where the head of the ventricular assist blood pump is lower than a shutoff head of the ventricular assist blood pump by 20 mmHg in pressure at a fixed rotational speed of the rotational part.

2. The ventricular assist blood pump according to claim 1, wherein
a relationship between the head of the ventricular assist blood pump and the flow rate of the ventricular assist blood pump is measured using the liquid whose viscosity and density correspond to viscosity and density of blood as the working liquid, and in a graph where the head of the ventricular assist blood pump is taken on the axis of ordinates using mmHg as a unit and the flow rate of the ventricular assist blood pump is taken on the axis of abscissas using L/min as a unit, the inclination of the graph is set to a value which falls within a range of −5 to 0 at a point where the head of the ventricular assist blood pump is set to 100 mmHg and the flow rate of the ventricular assist blood pump is set to 5 L/min at the fixed rotational speed.

3. The ventricular assist blood pump according to claim 1, wherein
a change in the flow rate of the ventricular assist blood pump is large with respect to a change in the head of the ventricular assist blood pump when the liquid is made to flow in the ventricular assist blood pump with a rotational speed of the rotational part set to a fixed value.

4. The ventricular assist blood pump according to claim 1, wherein
the liquid whose viscosity and density correspond to viscosity and density of blood is used as the working liquid, and when a pressure loss is measured in a state where the ventricular assist blood pump is stopped and the flow rate of the ventricular assist blood pump is set to 6 L/min, the pressure loss is 20 mmHg or less.

5. The ventricular assist blood pump according to claim 1, wherein
the first numerical value obtained by dividing the volume of the rotational part by the capacity of the housing falls within a range of 0.06 to 0.12.

6. The ventricular assist blood pump according to claim 1, wherein
a minimum gap between the impeller and an inner wall of the housing during the operation of the ventricular assist blood pump falls within a range of 0.1 mm to 2.0 mm.

7. The ventricular assist blood pump according to claim 1, wherein
the ventricular assist blood pump is formed of a centrifugal-type ventricular assist blood pump, and a second numerical value obtained by dividing a minimum inner diameter of a blood introducing portion of the ventricular assist blood pump by a diameter of rotation of the impeller is set to a value which falls within a range of 0.2 to 0.8.

8. The ventricular assist blood pump according to claim 1, wherein
the ventricular assist blood pump is formed of a centrifugal-type ventricular assist blood pump, and a third numerical value obtained by dividing a minimum inner diameter of a blood delivering portion of the ventricular assist blood pump by a diameter of rotation of the impeller is set to a value which falls within a range of 0.2 to 0.8.

9. The ventricular assist blood pump according to claim 1, wherein
a difference between a maximum flow rate of the liquid and a minimum flow rate of the liquid in a state where the ventricular assist blood pump is connected to a liquid-discharge source which discharges the liquid while increasing and decreasing a flow rate of the liquid at a fixed cycle is 40% or more of a difference between the maximum flow rate of the liquid and the minimum flow rate of the liquid in a state where the ventricular assist blood pump is not connected to the liquid-discharge source.

10. The ventricular assist blood pump according to claim 9, wherein
the difference between the maximum flow rate of the liquid and the minimum flow rate of the liquid in the state where the ventricular assist blood pump is connected to the liquid-discharge source is 80% or more of the difference between the maximum flow rate of the liquid and the minimum flow rate of the liquid in the state where the ventricular assist blood pump is not connected to the liquid-discharge source.

11. The ventricular assist blood pump according to claim 4, wherein
the pressure loss falls within a range of 5 mmHg to 16 mmHg.

12. The ventricular assist blood pump according to claim 1, wherein
a difference between a maximum flow rate of the ventricular assist blood pump and a minimum flow rate of the ventricular assist blood pump in a state where the ventricular assist blood pump is connected to a liquid-discharge source which discharges the liquid while increasing and decreasing a flow rate of the liquid at a fixed cycle is 200% or more of the difference between a maximum flow rate of the liquid and a minimum flow rate of the liquid in a state where the ventricular assist blood pump is not connected to the liquid-discharge source.

\* \* \* \* \*